(12) United States Patent
Grez

(10) Patent No.: US 9,775,976 B2
(45) Date of Patent: Oct. 3, 2017

(54) SKIN CLEANSING APPARATUS WITH OSCILLATION MOTION CONVERTER

(71) Applicant: L'Oreal, Paris (FR)

(72) Inventor: Joseph Grez, North Bend, WA (US)

(73) Assignee: L'Oreal, Paris (FR)

(*) Notice: Subject to any disclaimer, the term of this patent is extended or adjusted under 35 U.S.C. 154(b) by 579 days.

(21) Appl. No.: 14/109,798

(22) Filed: Dec. 17, 2013

(65) Prior Publication Data

US 2015/0165179 A1   Jun. 18, 2015

(51) Int. Cl.
*A61H 23/02* (2006.01)
*A61M 35/00* (2006.01)

(52) U.S. Cl.
CPC ........... *A61M 35/003* (2013.01); *A61H 23/02* (2013.01); *A45D 2200/1054* (2013.01); *A45D 2200/1063* (2013.01)

(58) Field of Classification Search
CPC .......... A61H 7/002; A61H 7/004; A61H 7/00; A61H 23/02; A61H 23/0218; A61H 23/0254; A61H 2023/029; A61H 2201/1481; A61H 2201/149; A45D 34/04; A45D 34/042; A45D 34/043; A45D 34/045; A46B 13/008; A46B 13/023; A46B 13/026; A46B 13/02; A46B 13/04; A46B 13/06
See application file for complete search history.

(56) References Cited

U.S. PATENT DOCUMENTS

| | | | | |
|---|---|---|---|---|
| 4,203,431 A * | 5/1980 | Abura | A61H 7/005 | 15/28 |
| 5,345,640 A * | 9/1994 | Goss | A46B 13/04 | 15/21.1 |
| 5,458,561 A * | 10/1995 | Schweisfurth | A61H 15/0092 | 601/119 |
| 7,386,906 B2 * | 6/2008 | Roth | A46B 13/06 | 15/21.1 |
| 7,789,092 B2 * | 9/2010 | Akridge | A61B 17/50 | 132/200 |
| 8,398,569 B1 * | 3/2013 | Mortimer | A61H 23/0263 | 601/46 |
| 2013/0060176 A1 * | 3/2013 | Nichols | A46B 13/023 | 601/137 |
| 2015/0034113 A1 * | 2/2015 | Yamagishi | A46B 13/02 | 132/200 |

* cited by examiner

*Primary Examiner* — Justine Yu
*Assistant Examiner* — Michael Tsai
(74) *Attorney, Agent, or Firm* — Clark A. Puntigam; Jensen & Puntigam, P.S.

(57) ABSTRACT

An appliance for facial skin applications having a drive assembly with an oscillating drive shaft. A base member is removably attachable to the oscillating drive member and an infuser member includes a soft tip with a concave surface adapted to hold a skin formulation for infusing into the skin of the user. A spring assembly connects the base member to the infuser member, and is arranged to convert the oscillating action of the drive shaft and the base member to an action having a significant axial component, toward and away from the skin, to produce an infusing action on the skin.

27 Claims, 4 Drawing Sheets

SKIN CLEANSING APPARATUS WITH OSCILLATION MOTION CONVERTER

TECHNICAL FIELD

This invention relates generally to a skin cleansing appliance with an oscillating drive member and more specifically concerns an oscillation conversion mechanism connectable to the drive member, the conversion mechanism producing an axial action, suitable for infusing a skin formulation.

BACKGROUND OF THE INVENTION

Various skin cleansing brush appliances are known which produce an oscillating brush action, such as disclosed in U.S. Pat. No. 7,320,691, the contents of which are hereby incorporated by reference. In this particular appliance, the brushhead surface oscillates back and forth through a selected angle, typically in the range of 7-15°, and at a frequency of 176 Hz. This action produces a cleansing action on the skin.

In another skin treatment appliance, a skin formulation is infused into the skin by back-and-forth action, toward and away from the skin, such as disclosed in U.S. Pat. No. 8,469,909, the contents of which are also hereby incorporated by reference. This particular appliance includes an applicator tip assembly which includes a relatively stiff base for connecting to a drive member, and a softer tip portion, which may be configured to hold a dose or so of a skin formulation. This appliance, for example, uses a frequency of approximately 120 Hz and an amplitude of approximately 0.1 inches.

It would be desirable to develop a motion conversion mechanism having a base portion which can be removably connected to the oscillating drive member of a skin cleansing brush, so that a single driving appliance can be used for both skin cleansing and skin treatment by infusing a skin formulation.

SUMMARY OF THE INVENTION

Accordingly, one aspect of the present invention is an appliance for use in facial skin applications, comprising: an appliance body which includes a drive assembly, a source of power for the drive assembly, a user-controlled on/off member, and a drive shaft member at a distal end of the drive assembly, operating in an oscillating manner about an appliance axis; a motion converter comprising a base member removably attachable to the drive shaft member, an infuser member which includes a portion configured and adapted to hold a skin formulation and to infuse the formulation into the skin of a user; and a spring assembly connecting the base member to the infuser member, which converts the oscillating action of the drive shaft and the base member to an infuser action having a significant axial component, toward and away from the skin, approximately parallel to said appliance axis.

Another aspect of the present invention includes a motion converter assembly adapted to removably fit on an appliance used for facial skin applications, the appliance including an appliance body which includes a drive assembly, a source of power for the drive assembly, a user controlled on/off member, and a drive shaft member at the distal end of drive assembly, oscillating about an appliance axis, wherein the motion converter comprises: a base member removably attachable to the drive shaft member; an infuser member which includes a tip portion configured and adapted to hold a skin formulation and to infuse the formulation into the skin of the user; and a spring assembly connecting the base member to the infuser member which converts the oscillating action of the drive shaft and the base member to an infuser action having a significant axial component, toward and away from the skin, approximately parallel to said appliance axis.

BRIEF DESCRIPTION OF THE DRAWINGS

FIGS. 5A-5D are horizontal cross-sectional diagrams of motion conversion mechanisms having one, two, three and four spring members, respectively, while

BEST MODE FOR CARRYING OUT THE INVENTION

Figure 1:
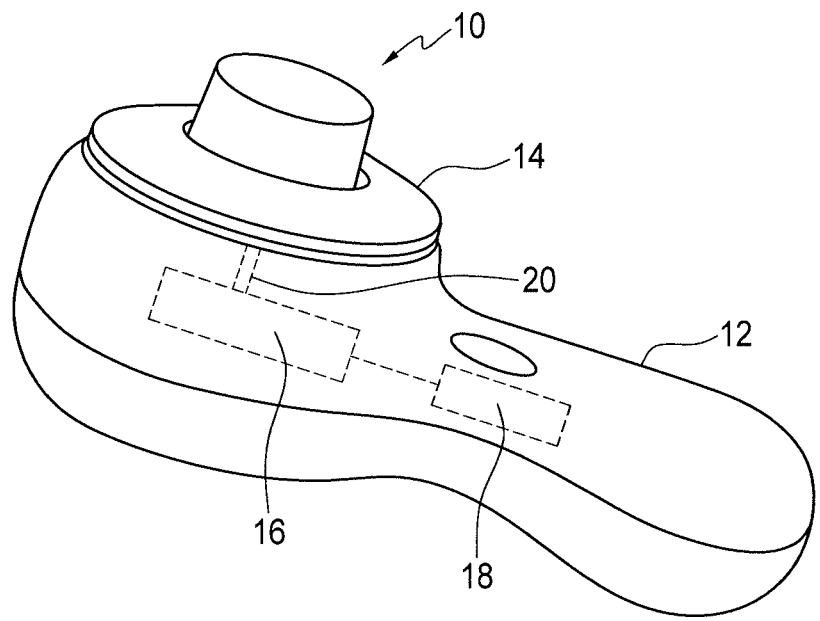
FIG. 1 is a perspective view of a dual action appliance which includes a motion conversion mechanism.
Figure 2:
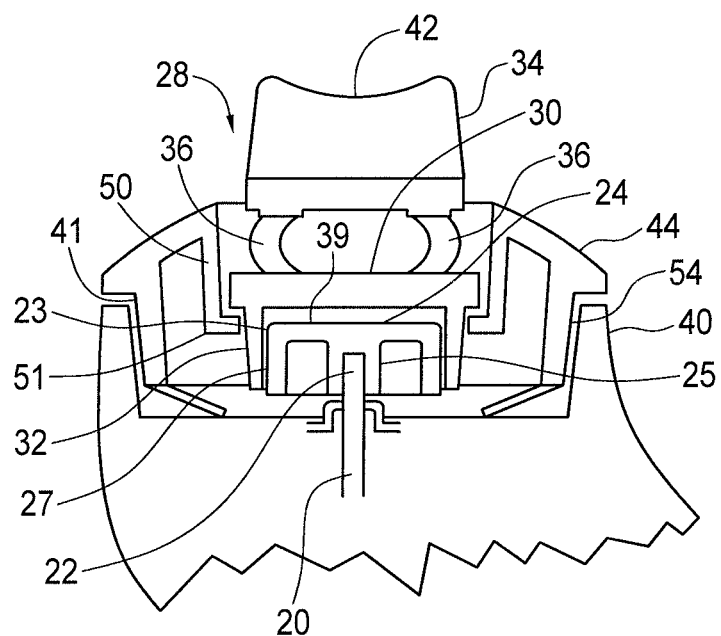
FIG. 2 is a lateral cross-sectional view through the head end of the appliance of FIG. 1.

FIG. 1 is a perspective view of a conventional skin brush appliance shown generally at 10, with a motion conversion mechanism secured to the drive member. It includes a handle portion 12 and an adjacent head portion 14. Contained within the handle portion is a drive assembly shown generally at 16 and a power source, such as a rechargeable battery, at 18. The drive assembly can take various forms, with a drive shaft 20 extending from the drive assembly vertically within head portion 14. Drive assembly 16 produces an oscillating-type action of drive shaft 20. In one skin brush arrangement, the angle of oscillation is within the range of 5-15°, while the frequency is in the range of 80-200 Hz. Both of these values can be varied depending on the particular application. Referring to FIG. 2, mounted on a distal end 22 of drive shaft 20 is a drive element 24. Drive element 24 has a central portion 25 which is permanently fixed to drive shaft 20.

A motion converter is shown generally at 28. The motion converter includes a plate-like base portion 30 which is typically made of stiff plastic. Base portion 30 is typically circular in configuration, approximately one inch in diameter and approximately 0.1 inch thick, although these dimensions can be varied. Extending downwardly from base portion 30 are a plurality of legs 32 or alternatively a circular ring which are angled and otherwise adapted to snap onto depending circumferential portion 27 of drive element 24, with a frictional fit, so that as drive element 24 oscillates, so does base portion 30. An upper infuser portion 34 of motion converter 28 is positioned above base portion 30. Connecting base portion 30 to infuser portion 34 are one or more spring members 36. The upper infuser portion has a soft tip with a concave upper surface 42, although other configurations are possible and may be conveniently used.

In the embodiment shown, infuser portion 34 is approximately one inch in diameter and has a height of approximately 0.5 inch at the periphery thereof. The concave upper surface 42 is adapted in the preferred embodiment to hold a single dose of a selected skin formulation, although this arrangement can be varied to hold less or more of a skin formulation.

The spring members 36 are resilient plastic and in the embodiment shown are cylindrical, approximately 0.1 inch in diameter. Alternatively and preferably, they can be flat metal springs, with a width dimension of 0.1-0.2 inch and a thickness of 0.1 mm to 0.4 mm. Several spring members can be used.

Referring again to FIG. 2, a mounting ring 44 extends between the motion conversion mechanism and a peripheral lip 40 of head portion 14 of the appliance. In the embodiment shown, peripheral lip 40 is approximately 0.1 inch high, so that an upper surface 39 of drive element 24, when it is positioned operatively on drive shaft 20, is slightly below the upper edge of the peripheral lip. The mounting ring 44 is circular and includes a first depending element 50 from an inner edge of the mounting ring element 44, including a small, inwardly extending lip 51 which comes close to but does not contact the depending circumferential portion of the base portion of the motion conversion mechanism. The mounting ring 44 includes a second depending circumferential element 54 which comes adjacent the interior surface of the peripheral lip of the head portion of the appliance and then angles inwardly a short distance at the lower end of element 54. The periphery of the mounting element fits over the upper edge of the peripheral lip 40 of the head portion. The mounting ring thus fills the space between the motion converter and the peripheral lip of the head portion.

The configuration and position of the spring members 36 of the motion conversion mechanism produces a change of motion such that the infuser portion moves generally axially (in and out relative to the head portion), with a small twisting component, while the base portion oscillates, following the action of the drive member. The resulting overall motion is oscillating with a twisting component. For example, the axial motion could be 240 Hz with the twisting action at 170 Hz. Alternatively, the motion converter could be designed by adjusting the rotary (twisting) mode relative to the driving frequency.

Figure 3:
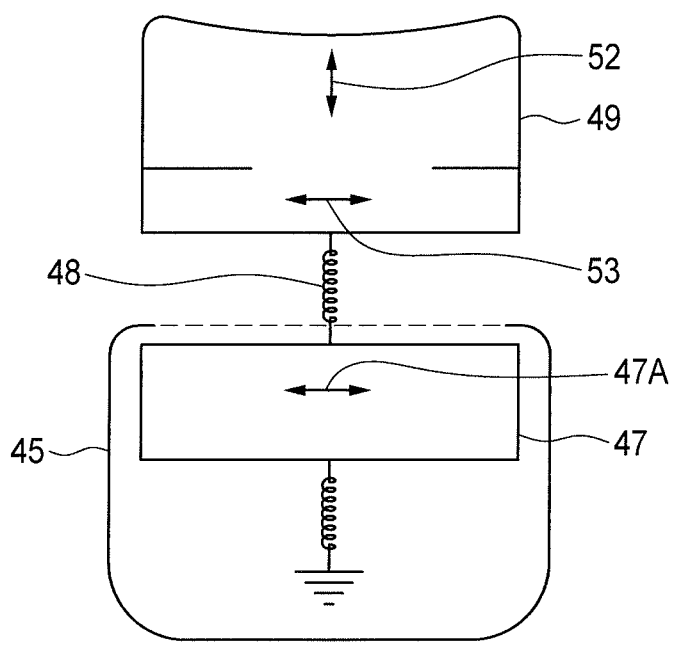
FIG. 3 is a cross-sectional view showing the dynamic response of the motion conversion mechanism.

Referring now to FIG. 3, which shows the dynamic response of the motion converter, as the drive element oscillates at its selected frequency, e.g. 176 Hz, the base portion, represented at 47, within head portion 45 of the motion converter, also rotates correspondingly, as represented by arrows 47A. The spring members, represented at 48, produce an action on the infuser portion, represented at 49, which is primarily in the vertical or axial direction, shown at 50, at approximately the same frequency or a multiple thereof, as the rotational action. It does typically, but not necessarily, include a slight rotating motion, shown at 51, although the primary motion is in the axial direction. In the embodiment shown, the axial motion is in the range of 0.01-0.2 inch. It is the arrangement and configuration of the spring members which produce the motion conversion action. The result is that a conventional skin brush appliance providing an oscillating action and a skin cleansing action with the brushhead can also be used to produce an axial action and a formulation infusing function.

Figure 4:
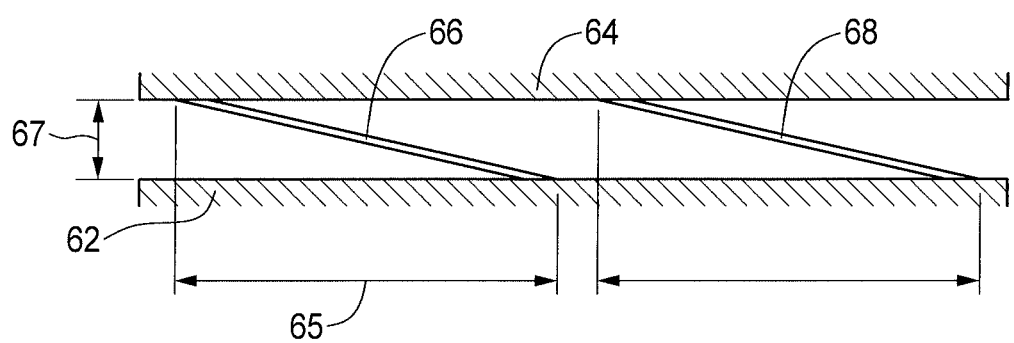
FIG. 4 is a circumferential view of a two-spring embodiment.
Figure 5A:
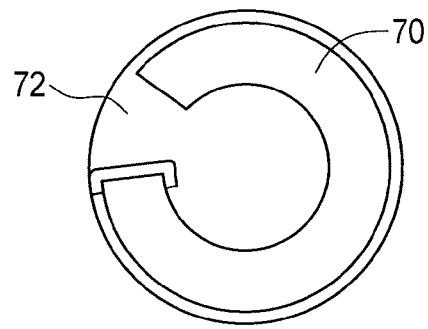
Figure 5B:
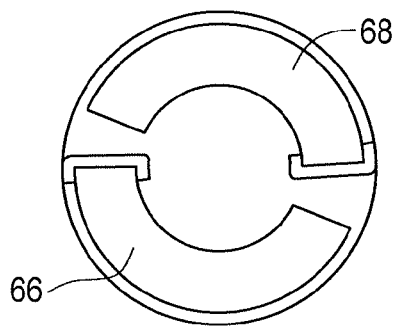
Figure 5C:
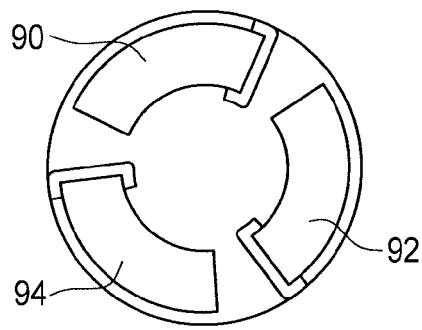
Figure 5D:
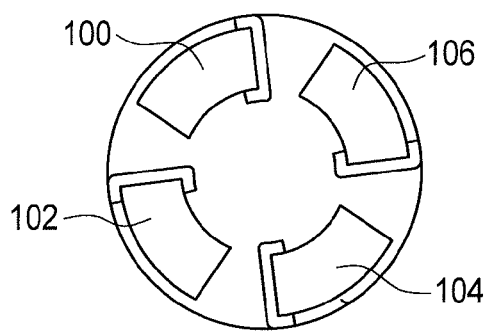
Figure 5E:
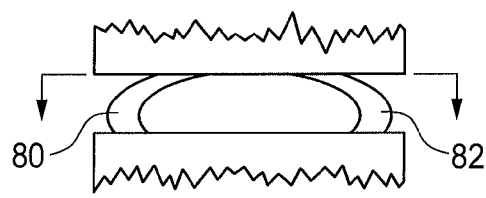
FIG. 5E is a vertical cross-sectional view of the two-spring embodiment.
Figure 6A:
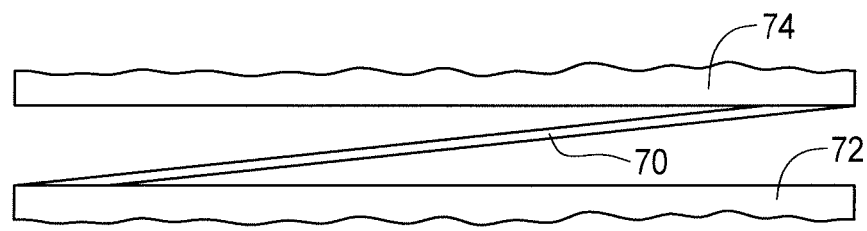
FIGS. 6A-6C are circumferential views of one-spring, three-spring and four-spring embodiments.
Figure 6B:
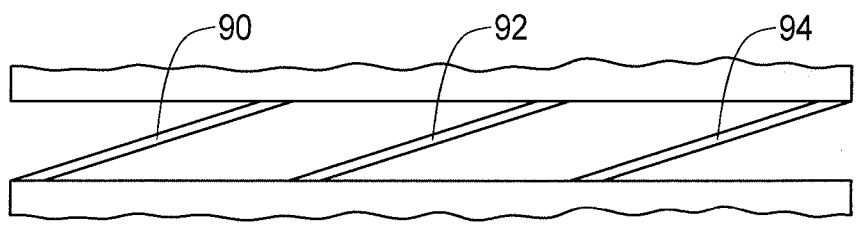
Figure 6C:
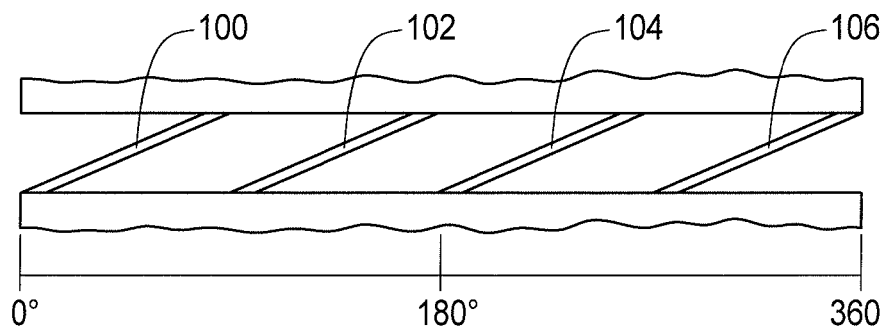

FIG. 4 shows an unwrapped, i.e. planar, circumferential view of a two-spring arrangement between the lower and upper portions of the motion converter. FIGS. 6A-6C show similar one-spring, three-spring and four-spring circumferential views. Referring specifically to FIG. 4, the upper surface 62 of the base portion and the lower surface 64 of the infuser portion are connected by two spring elements 66 and 68. In the embodiment shown, the two spring elements are separated by approximately 180° (FIG. 5B) and extend for approximately slightly less than half the circumference of the motion converter. The ends of spring elements extend from approximately the peripheries of the two portions a small distance inwardly of the two portions. The springs in FIGS. 5A-5E are flat metal springs. If the diameter of the motion converter is 1.2 inches, the total circumference will be 3.8 inches, which is shown in planar form in the drawings. The length of the spring elements compared to the distance between the infuser and base surfaces should be greater than 1, and preferably between 3-4 in order to satisfy dynamic conditions and produce the desired action in each case. This will determine the angle of the spring from the base portion and the infuser portion in each case.

FIGS. 6A-6C show similar arrangements for one-spring, three-spring and four-spring embodiments. The springs change in length, depending on the number of springs. FIGS. 5A-5E can be viewed in combination with FIGS. 6A-6C. The embodiments of FIGS. 5A and 6A include one spring 70 between the base portion 72 and the infuser portion 74 for a circumferential angle (FIG. 6A) of approximately 300°. FIG. 5A is the planar (unwrapped) circumferential view of FIG. 6A. FIGS. 3 and 5B show an embodiment with two springs 66 and 68, which oppose each other and extend over a circumferential angle of approximately 160°. FIGS. 5C and 6B show an embodiment with three equally spaced spring elements 90, 92 and 94, each spring extending for a circumferential angle of approximately 100°. FIGS. 5D and 6C show an embodiment with four springs 100, 102, 104 and 106, the springs being equally spaced and extending for a circumferential angle of approximately 80°. In each case, the respective ends of the springs are fixed to the base portion and the infuser portion, with a width of approximately one-half of the radius of the two portions, as shown in FIGS. 6A-6D, although this arrangement can be varied.

The functional result is that the oscillating action of the appliance drive shaft converted into axial action, albeit with a rotational component, which produces an infusing function for a skin formulation. The axial resonance of motion of the infuser portion, in response to its inertia combined with the spring rate of the springs, is a multiple of the driving frequency to produce the desired result. In other arrangements, the rotational component can be at or near zero. A single drive appliance can thus be used for both skin cleansing and formulation infusing depending upon the particular head member used, either a brushhead in one case and the motion conversion member disclosed herein in the other case.

Although a preferred embodiment of the invention has been disclosed for purposes of illustration, it should be understood that various changes, modifications and substitutions may be incorporated in the embodiment without departing from the spirit of the invention, which is defined by the claims which follow.

What is claimed is:

1. An appliance for use in facial skin applications, comprising:
   an appliance body which includes a drive assembly, a source of power for the drive assembly, a user-controlled on/off member, and a drive shaft member at a distal end of the drive assembly, operating in an oscillating manner about an appliance axis;
   a motion converter comprising a base member removably attachable to the drive shaft member, an infuser member which includes a tip portion configured and adapted to hold a formulation and to infuse said formulation into the skin of a user; and
   a spring assembly connecting the base member to the infuser member, comprising at least two spring members which extends over a selected circumferential angle between the base member and the infuser member, to convert the oscillating action of the drive shaft and the base member to an infuser action having a significant axial component, toward and away from the skin, approximately parallel to said appliance axis.

2. The appliance of claim 1, wherein the tip portion is flexible and has a concave configuration to hold the formulation.

3. The appliance of claim 2, wherein the flexible tip is a soft plastic or rubber, approximately one inch in diameter.

4. The appliance of claim 1, wherein the drive member oscillates at a frequency in the sonic frequency range.

5. The appliance of claim 4, wherein the axial oscillating frequency is between 80 and 200 Hz.

6. The appliance of claim 1, wherein the spring assembly includes two opposing spring elements, approximately 180° apart.

7. The appliance of claim 6, wherein the length of each spring to the separation between the two motion converter members is a ratio greater than 1.

8. The appliance of claim 7, wherein the ratio is in the range of 3-4.

9. The appliance of claim 1, wherein the respective ends of the spring members extend from approximately the peripheral edge of the base member and the infuser member inwardly a distance approximately one-half of the radius of the base member and infuser member.

10. The appliance of claim 1, wherein the spring assembly comprises one spring, which extends circumferentially for an angle of approximately 300°.

11. The appliance of claim 1, wherein the spring assembly includes two opposing springs, each spring extending for a circumferential angle of approximately 160°.

12. The appliance of claim 1, wherein the spring assembly includes three equally spaced springs, each spring extending for a circumferential angle of approximately 100°.

13. The appliance of claim 1, wherein the spring assembly includes four substantially equally spaced spring members, each spring member extending for a circumferential angle of approximately 80°.

14. The appliance of claim 1, wherein the infuser action has a small oscillating component, with the remaining action being axial.

15. A motion converter assembly adapted to removably fit on an appliance used for facial skin applications, the appliance including an appliance body which includes a drive assembly, a source of power for the drive assembly, a user controlled on/off member, and a drive shaft member at the distal end of the drive assembly, oscillating about an appliance axis, wherein the motion converter comprises:
a base member removably attachable to the drive shaft member;
an infuser member which includes a tip portion configured and adapted to hold a formulation and to infuse said formulation into the skin of the user; and
a spring assembly connecting the base member to the infuser member, comprising at least two spring members which extends over a selected circumferential angle between the base member and the infuser member, to convert the oscillating action of the drive shaft and the base member to an infuser action having a significant axial component, toward and away from the skin, approximately parallel to said appliance axis.

16. The motion converter of claim 15, wherein the tip portion is flexible and has a concave configuration to hold the formulation.

17. The motion converter of claim 16, wherein the flexible tip holds approximately one dose of a selected skin formulation.

18. The motion converter of claim 16, wherein the tip is a soft plastic or rubber, approximately one inch in diameter.

19. The motion converter of claim 15, wherein the spring assembly includes two opposing spring elements, approximately 180° apart.

20. The motion converter of claim 19, wherein the lower ends of the spring members extend from approximately the peripheral edge of the base member inwardly a distance of approximately one-half of the radius of the base member.

21. The motion converter of claim 15, wherein a ratio of the length of the springs to a separation distance between the base and infuser members is greater than 1.

22. The motion converter of claim 21, wherein the ratio is in the range of 3-4.

23. The motion converter of claim 15, wherein the spring assembly comprises one spring, which extends circumferentially for an angle of approximately 300°.

24. The motion converter of claim 15, wherein the spring assembly includes three equally spaced springs, each spring extending for a circumferential angle of approximately 100°.

25. The motion converter of claim 15, wherein the spring assembly includes four substantially equally spaced springs, each spring extending for a circumferential angle of approximately 80°.

26. An appliance kit for use in facial skin applications, comprising:
an appliance body which includes a drive assembly, a source of power for the drive assembly, a user-controlled on/off member, and a drive shaft member at a distal end of the drive assembly, operating in an oscillating manner about an appliance axis; and
a motion converter comprising a base member removably attachable to the drive shaft member, an infuser member which includes a tip portion configured and adapted to hold a skin formulation and to infuse said formulation into the skin of a user; and a spring assembly connecting the base member to the infuser member, comprising at least two spring members which extends over a selected circumferential angle between said base member and said infuser member, to convert the oscillating action of the drive shaft and the base member to an infuser action having a significant axial component, toward and away from the skin, approximately parallel to said appliance axis.

27. The appliance of claim 26, wherein the tip portion is flexible and has a concave configuration to hold said skin formulation.

* * * * *